United States Patent
Strongwater

(10) Patent No.: US 9,886,548 B2
(45) Date of Patent: Feb. 6, 2018

(54) MEDICAL DATA SYSTEM AND METHOD

(71) Applicant: Ironwood Medical Information Technologies, LLC, Bedford, NY (US)

(72) Inventor: Richard Strongwater, Bedford, NY (US)

(73) Assignee: IRONWOOD MEDICAL INFORMATION TECHNOLOGIES, LLC, Bedford, NY (US)

( * ) Notice: Subject to any disclaimer, the term of this patent is extended or adjusted under 35 U.S.C. 154(b) by 717 days.

(21) Appl. No.: 14/457,956

(22) Filed: Aug. 12, 2014

(65) Prior Publication Data

US 2015/0046190 A1 Feb. 12, 2015

Related U.S. Application Data

(60) Provisional application No. 61/864,916, filed on Aug. 12, 2013, provisional application No. 61/940,055, filed on Feb. 14, 2014.

(51) Int. Cl.
*G06Q 10/00* (2012.01)
*G06Q 50/00* (2012.01)
(Continued)

(52) U.S. Cl.
CPC ...... *G06F 19/322* (2013.01); *G06F 17/30297* (2013.01); *G06F 17/30312* (2013.01);
(Continued)

(58) Field of Classification Search
CPC .......................... G06F 19/322; G06F 17/30297
See application file for complete search history.

(56) References Cited

U.S. PATENT DOCUMENTS 7,509,263 B1 3/2009 Fiedotin et al.
7,539,684 B2 5/2009 Gogolak
(Continued)

FOREIGN PATENT DOCUMENTS

CN 101425109 5/2009
CN 102024027 4/2011
(Continued)

*Primary Examiner* — Christopher L Gilligan
(74) *Attorney, Agent, or Firm* — Leason Ellis LLP

(57) ABSTRACT

The present application regards a system and method including database(s) of medical records, processed medical records, user profile information and electronic medical information including information associated with medical terminology associated with diagnoses, treatments and evaluations. A first user interface module is configured to provide prompts for information regarding electronic medical information, and to receive and store responses to the prompts. Further, an electronic medical record processing module converts a medical record into a processed medical record. Further, a second user interface module displays the processed medical record and at least some corresponding information to a first user in accordance with electronic user profile information associated with the first user, and displays the processed medical record and at least some different corresponding information regarding at least one different medical term from the medical record to a second user in accordance with user profile information associated with the second user.

20 Claims, 13 Drawing Sheets

(51) Int. Cl.
*G06F 19/00* (2011.01)
*G06F 17/30* (2006.01)
*H04L 29/08* (2006.01)

(52) U.S. Cl.
CPC ........ *G06F 19/324* (2013.01); *G06F 19/3418* (2013.01); *G06F 19/3431* (2013.01); *H04L 67/306* (2013.01)

(56) References Cited

U.S. PATENT DOCUMENTS

| | | |
|---|---|---|
| 7,593,913 B2 | 9/2009 | Wang et al. |
| 7,856,365 B2 | 12/2010 | Fiedotin et al. |
| 7,945,454 B2 | 5/2011 | Firozvi |
| 8,131,769 B2 | 3/2012 | Gogolak et al. |
| 8,150,750 B2 | 4/2012 | Ray |
| 8,643,648 B2 | 2/2014 | Heywood et al. |
| 8,694,555 B2 | 4/2014 | Gogolak et al. |
| 2001/0042080 A1 | 11/2001 | Ross |
| 2003/0144877 A1 | 7/2003 | Goldmann et al. |
| 2004/0243546 A1 | 12/2004 | Boone et al. |
| 2005/0251423 A1 | 11/2005 | Bellam et al. |
| 2007/0185737 A1* | 8/2007 | Friedlander ............ G06Q 50/24 705/3 |
| 2007/0288519 A1 | 12/2007 | Ford |
| 2008/0255883 A1* | 10/2008 | Jones ...................... G06Q 10/10 705/3 |
| 2010/0131282 A1* | 5/2010 | Rowe ...................... G06Q 10/06 705/2 |
| 2010/0145731 A1 | 6/2010 | Benja-athon |
| 2010/0274584 A1 | 10/2010 | Kim |
| 2011/0238447 A1* | 9/2011 | Miglietta .............. G06F 19/322 705/3 |
| 2011/0270843 A1 | 11/2011 | Albin |
| 2012/0226113 A1 | 9/2012 | Pandya |
| 2013/0041685 A1 | 2/2013 | Yegnanarayanan |
| 2014/0136219 A1* | 5/2014 | Lee ....................... G06F 19/322 705/2 |

FOREIGN PATENT DOCUMENTS

| | | |
|---|---|---|
| CN | 103513781 | 1/2014 |
| CN | 103544383 | 1/2014 |

* cited by examiner

RE: Louis

Dear Dr.

In followup to my original letter of May 1, _____ regarding Louis. He does have the prothrombin gene mutation, heterozygous. This is generally viewed as a venous risk factor only and will not be actionable for alternative anticoagulation. He does not have aspirin resistance. He had confirmation of an increased titer IgG cardiolipin antibody this time at Quest Lab being similar to the earlier value at 35 GPL, intermediate titer. He had an indeterminate lupus anticoagulant. His D-dimer level is slightly high at 0.53 mcg/mL.

In sum, he has subtle evidence of clotting activation and indeed has a possible diagnosis of antiphospholipid syndrome. There is a consideration of anticoagulation therapy being added to his aspirin. I view this as a difficult decision making in this context. This will have to be discussed with his cardiologist given his or her specialized knowledge in his coronary events. I will be glad to discuss these issues further as needed. Reasonable consideration is low-target INR, i.e. 1.8 along with the aspirin.

Sincerely,

Fig. 10

Risk factors that worsen disease:
In heterozygous state in patients with venous thrombosis, the defect is not a reason for long term anticoagulation per se, but in combination with an OCP, or the postpartum state or other thrombophilic states, can be additive or synergistic to risk.

MEDICAL DATA SYSTEM AND METHOD

CROSS-REFERENCE TO RELATED APPLICATIONS

The present application claims priority to U.S. Provisional Patent Application No. 61/864,916, filed Aug. 12, 2013, and U.S. Provisional Patent Application No. 61/940,055, filed Feb. 14, 2014, which are hereby incorporated by reference in their respective entireties.

BACKGROUND

Medical information is provided in a plethora of formats and from many sources. Despite technological advances regarding access to information, it remains extremely difficult to manage the many volumes of information and provide effective care for patients.

The present application addresses these and other considerations.

SUMMARY OF THE INVENTION

In one or more implementations, the present application includes an apparatus and method that include at least one database that is accessible to at least one processor. The database(s) include electronic medical records including information associated with one or more of medical diagnoses, treatments and evaluations of respective patients. Additionally, the database(s) include electronic processed medical records that include at least some of each electronic medical record in a selectable format, wherein the selectable format provides corresponding information regarding at least one medical term; electronic user profile information identifying respective users and representing corresponding degrees understanding of medical information for each of the respective users; electronic medical information including information associated with medical terminology associated with the diagnoses, treatments and evaluations. Moreover, a first user interface module is provided that is configured with at least one processor to provide prompts for information associated with the electronic medical information, and to receive responses to the prompts and to store the responses in the at least one database. Further, an electronic medical record processing module configured with at least one processor that is configured to convert a first electronic medical record into a first electronic processed medical record that includes at least some of the first electronic medical record in a selectable format. Further, a second user interface module is provided that is configured with at least one processor to display the first electronic processed medical record and at least some corresponding information regarding at least one medical term from the first electronic medical record to a first user in accordance with electronic user profile information associated with the first user, and to display the first electronic processed medical record and at least some different corresponding information regarding at least one different medical term from the first electronic medical record to a second user in accordance with electronic user profile information associated with the second user.

These and other aspects, features, and advantages can be appreciated from the accompanying description of certain embodiments of the invention and the accompanying drawing figures and claims.

BRIEF DESCRIPTION OF THE DRAWINGS

FIG. 6 illustrates an example data entry display screen that is configured for users to enter information associated with medical terms in accordance with an implementation of the present application;

FIG. 9 illustrates an example data entry display screen that is configured for users to add and edit information associated with signs and symptoms that are associated with a respective medical term; and FIGS. 10-13 illustrate an example implementation of healthcare record graphical user interface in accordance with an implementation.

DETAILED DESCRIPTION OF CERTAIN EMBODIMENTS OF THE INVENTION

The present application regards a system and method that includes a computer-based tool to assist healthcare providers and other medical personnel, such as primary care physicians, to make accurate and cost-effective medical evaluations. The tool can aid in establishing the diagnoses of diseases and medical disorders, as well as to provide information regarding medical conditions and procedures. Such evaluation can be made on the basis of signs and symptoms described by patients or observed by physicians. A plurality of data sources can be accessed for populating one or more databases of medical health information. In one or more implementations, a "medical dictionary index" is provided for example, using respective medical terms, that provides an index to the database.

The present application regards, generally, management and display of medical information, including patient medical records, and more specifically, regards the generation and use of a new medical definitions and conditions database. The information stored in the database can include information representing one or more medical conditions, such as diseases, results of trauma, bacterial infections, viruses, parasites and congenital defects. The information may further include individual patient medical health records, such as relating to treatments, physician (or other healthcare provider) visits, medical tests and/or analysis thereof, or the like. Unlike known systems, in which complex medical terminology and meanings are referenced from many sources, the present application provides complex processing of various information to provide for convenient and usable analysis of the information.

Figure 1:
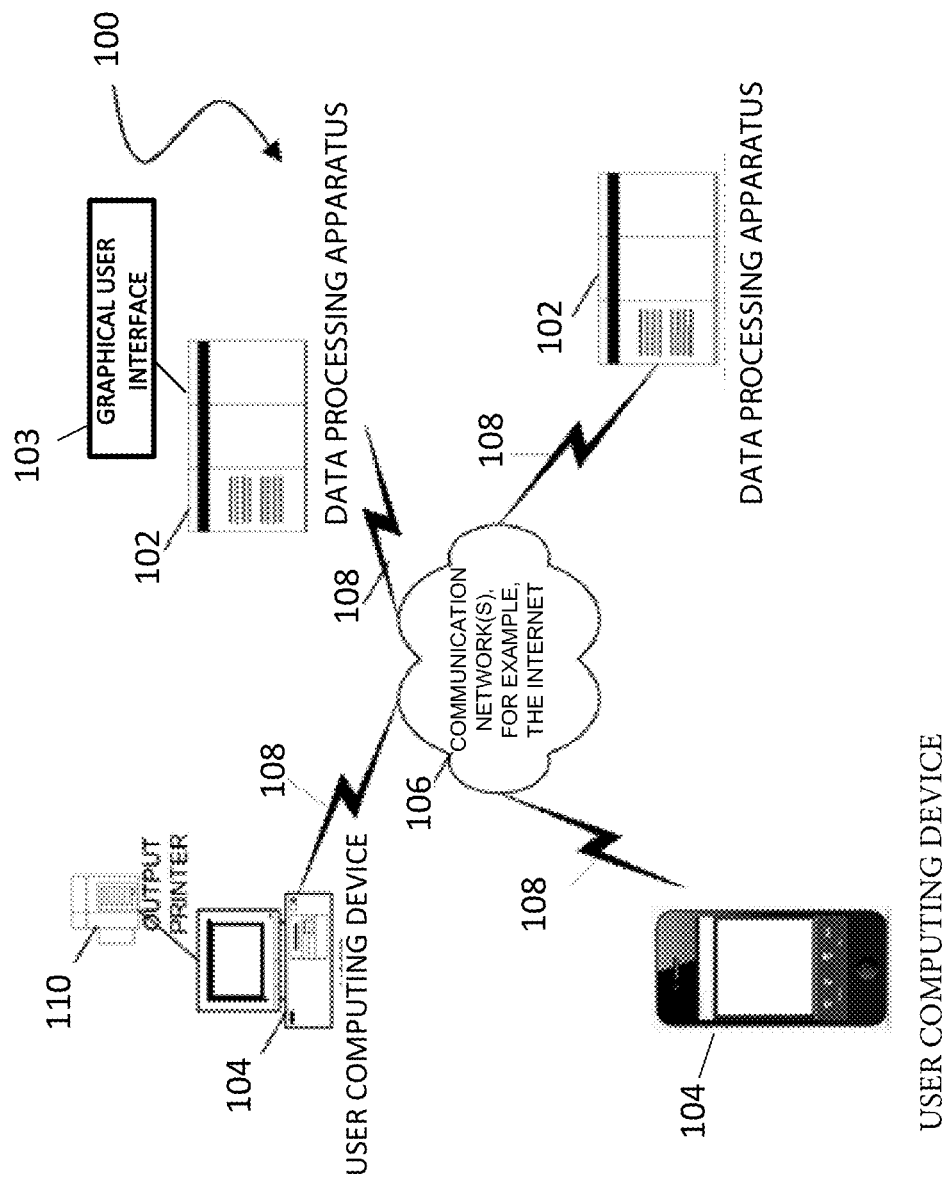
FIG. 1 is a block diagram illustrating an example implementation of the present application and that represents an association of a plurality of devices and the flow of information associated with the devices.

Referring to the drawings, in which like reference numerals refer to like elements, FIG. 1 is a block diagram illustrating an example implementation of the present application and that represents an association of a plurality of devices and the flow 108 of information associated with the devices. In the example shown in FIG. 1, various computing devices 102 and 104 are shown, each capable of executing desktop and/or mobile computing device web browser application(s) including INTERNET EXPLORER, CHROME, FIREFOX, and other (e.g., SAFARI, OPERA). In addition to standard web browser application functionality, user information can be gathered via Push Notifications, and information can be retrieved from a computing device using a "REST" interface. Various mobile devices running different operating systems are shown, including IOS, ANDROID and other (e.g., PALM, WINDOWS or other mobile device operating system).

In the example shown in FIG. 1, data processing apparatus 102 is operatively coupled to user computing devices 104. Devices 104 can be respectively operated by one or more healthcare providers and associated staff, medical specialists and/or consumers. Healthcare providers can include, for example, physicians, physician assistants, nurses, therapists and/or other providers of healthcare services. Data processing apparatus 102 and/or user computing device 104 can be operable to store various information including, for example, personal or identifying information about a user/patient, information identifying a respective computing device and/or software operating thereon, user activity (e.g., browsing history, medical history, information about a respective social network, social actions or activities, profession, preferences or a current location), or the like.

In addition, certain data can be treated in one or more ways before being stored or used, so that personally identifiable information is not displayed. For example, a person's identification number can be used to retrieve detailed information about a user, and which can be transmitted to a healthcare professional. The healthcare professional (or the specific employee or agent of the professional) may not be provided with personally identifiable information about the patient. In this way, a user's anonymity can be preserved, for example to maintain expectations of anonymity. Also illustrated in FIG. 1 is a network 106, which can be configured as a local area network (LAN), wide area network (WAN), Peer-to-Peer network ("P2P"), Multi-Peer network, the Internet, one or more telephony networks or a combination thereof, that is operable to connect data processing apparatus 102 and/or devices. Though many of the examples and implementations shown and described herein relate to product and/or service recommendations, many other forms of content can be provided and/or delivered by system 100.

Figure 2:
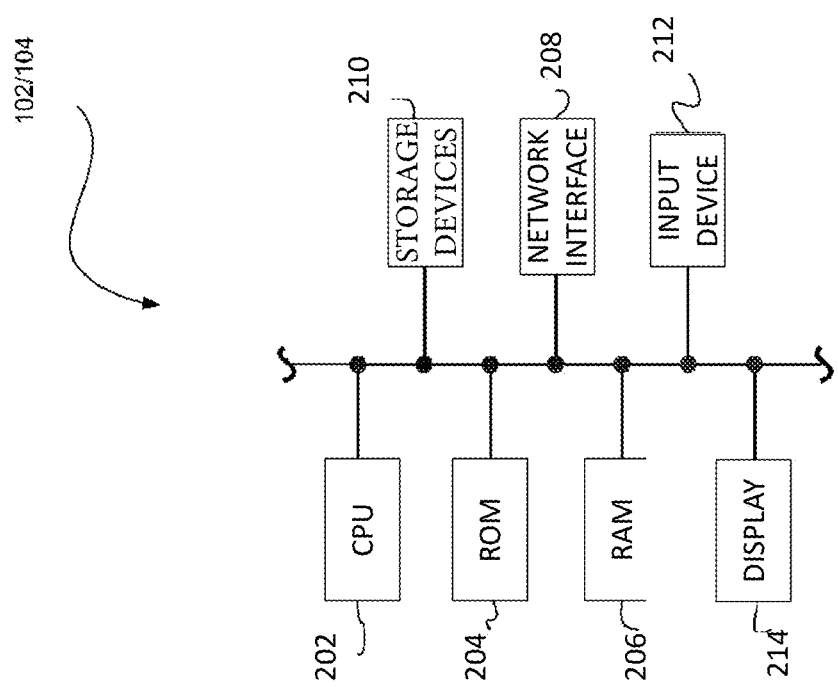
FIG. 2 is a block diagram that illustrates functional elements of one or more of data processing apparatus or computing device.

FIG. 2 is a block diagram that illustrates functional elements of one or more of data processing apparatus 102 or computing device 104 and preferably include one or more central processing units (CPU) 202 used to execute software code in order to control operations, including of data processing apparatus 102, read only memory (ROM) 204, random access memory (RAM) 206, one or more network interfaces 208 to transmit and receive data to and from other computing devices across a communication network, storage devices 210 such as a hard disk drive, solid state drive, floppy disk drive, tape drive, CD-ROM or DVD drive for storing program code, databases and application code, one or more input devices 212 such as a keyboard, mouse, track ball and the like, and a display 214.

The various components of devices 102 and/or 104 need not be physically contained within the same chassis or even located in a single location. For example, storage device 210 can be located at a site which is remote from the remaining elements of computing devices 102 and/or 104, and can even be connected to CPU 202 across communication network 106 via network interface 208.

The functional elements shown in FIG. 2 (designated by reference numbers 202-214) are preferably the same categories of functional elements preferably present in computing device 102 and/or 104. However, not all elements need be present, for example, storage devices in the case of PDAs, and the capacities of the various elements are arranged to accommodate expected user demand. For example, CPU 202 in computing device 104 can be of a smaller capacity than CPU 202 as present in data processing apparatus 102. Similarly, it is likely that data processing apparatus 102 will include storage devices 210 of a much higher capacity than storage devices 210 present in computing device 104. Of course, one of ordinary skill in the art will understand that the capacities of the functional elements can be adjusted as needed.

The nature of the present application is such that one skilled in the art of writing computer executed code (software) can implement the described functions using one or more or a combination of a popular computer programming language including but not limited to C++, VISUAL BASIC, JAVA, ACTIVEX, HTML, XML, ASP, SOAP, IOS, OBJECTIVE C, ANDROID, TORR and various web application development environments.

As used herein, references to displaying data on computing device 104 refer to the process of communicating data to the computing device 104 across communication network 106 and processing the data such that the data can be viewed on the user computing device 104 display 214 using a web browser, custom application or the like. The display screens on computing devices 102/104 present areas within system 100 such that a user can proceed from area to area within the system 100 by selecting a desired link. Therefore, each user's experience with system 100 will be based on the order with which (s)he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of system 100.

Although the present application is described by way of example herein in terms of a web-based system using web browsers, custom applications and a web site server (data processing apparatus 102), and with mobile computing devices, system 100 is not limited to that particular configuration. It is contemplated that system 100 can be arranged such that computing device 104 can communicate with, and display data received from, data processing apparatus 102 using any known communication and display method, for example, using a non-Internet browser Windows viewer coupled with a local area network protocol such as the Internetwork Packet Exchange (IPX). It is further contemplated that any suitable operating system can be used on computing device 104, for example, WINDOWS 3.X, WINDOWS 95, WINDOWS 98, WINDOWS 2000, WINDOWS CE, WINDOWS NT, WINDOWS XP, WINDOWS VISTAWINDOWS 7, WINDOWS 8, MAC OS, OSX, LINUX, IOS, ANDROID and any suitable PDA or palm computer operating system.

Figure 3:
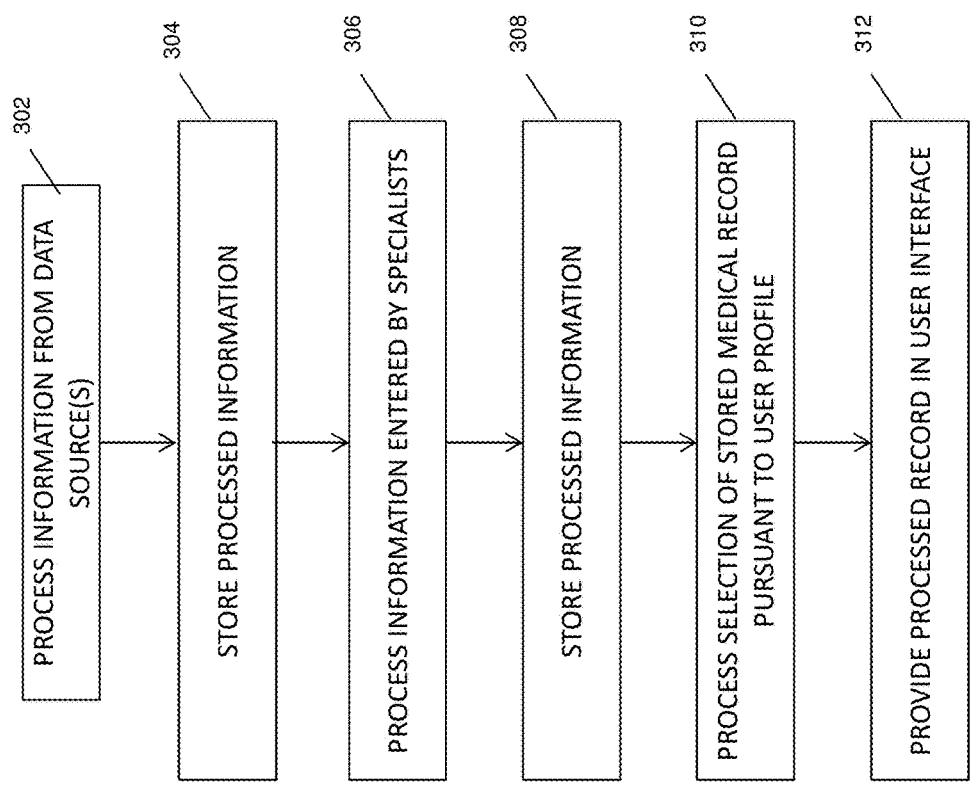
FIG. 3 is a flowchart of an example method for providing medical health records and corresponding functionality shown and described herein in accordance with an example implementation.

FIG. 3 is a flowchart of an example method for providing medical health records and corresponding functionality shown and described herein in accordance with an example implementation. In some implementations, the method can be performed by a processor executing instructions in a computer-readable storage medium. For example, the method can be performed by the data processing apparatus 102 and/or user computing device 104. It should be noted that while various operations described herein are illustrated with respect to individual webpages, such operations can be similarly employed with respect to groups or collections of webpages (e.g., websites). At step 302, information received from various data sources is processed. For example, information may be obtained vis-à-vis a screen capture process (as known in the art), an electronic file, such as PDF file, an image file, such as a JPEG, TIFF or other image format, a facsimile, a scanned document or other document source. The processing that occurs in step 302 can include converting from one format to another (e.g., image to text), and parsing a document for future comparison and/or analysis. Thereafter, the processed information is stored in one or more databases (step 304).

Continuing with reference to the flowchart shown in FIG. 3, at step 306 information that is entered by one or more users, such as specialists of a particular industry or practice, is processed. For example, a graphical user interface can be provided by data processing apparatus 102 and/or user computing device 104 that includes data entry display screens and graphical screen controls for users to submit topical information (see below, for example, and with reference to FIGS. 6-9). The topical information can be based upon, for example, industry-relevant key terms that have esoteric and complex meanings known well to industry specialists. In addition to providing definitions of the key terms, associated information, such as relating to causes, risks, diagnoses and treatment (in the case of medical information), can further be received and processed in step 306. For example, a cardio specialist is entering information associated with acute aortic dissection. A relatively brief definition is provided (e.g., 75 words) that describes the procedure, as well as a brief description of signs and symptoms associated with acute coronary syndrome. Other information received in the graphical user interface from the cardio specialist includes associated symptoms produced by malperfusion, including that relate to coronary, cerebrovascular, upper extremity, spinal cord, visceral, and lower extremity. In addition, the cardio specialist enters information associated with causes and risk factors, diagnostic workup information, treatment and follow-up information associated with acute aortic dissection. The information can be processed and stored (step 308) to be usable in a graphical user interface provided to another user, such as a family physician who would not be otherwise familiar with details associated with acute aortic dissection.

Continuing with reference to the flowchart shown in FIG. 3, at step 310 a selected stored medical record is processed pursuant to a user profile associated with the respective user to provide the medical record in a processed format in accordance with the teachings herein. For example, a family physician accesses a graphical user interface that includes a copy of the medical record with the term "acute aortic dissection" flagged or highlighted. Thus, as shown and described with reference to the flowchart in FIG. 3, information can be received from a plurality of sources, including via a graphical user interface that provides one or more data entry display screens, for processing and storing information. The information can, thereafter, be used to provide concise, accurate and up-to-date references for respective users and in respective contexts.

Figure 4:
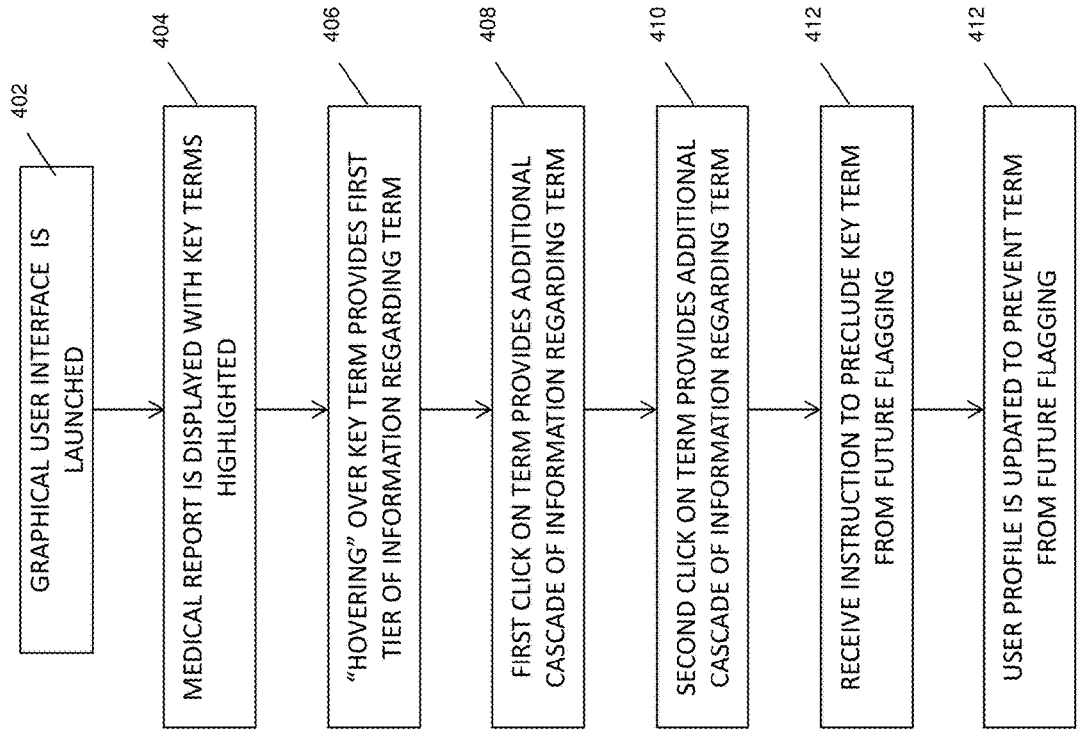
FIG. 4 is a flowchart of an example method for providing medical health records and corresponding functionality shown and described herein in accordance with an example implementation.

FIG. 4 is a flowchart of an example method for providing medical health records and corresponding functionality shown and described herein in accordance with an example implementation. At step 402, a healthcare provider, such as a doctor, initializes (e.g., "launches") the graphical user interface to review a medical report associated with a respective patient. At step 404, the medical report is displayed in the user interface with key terms highlighted. Any words of possible uncertainty that are in the database are flagged or highlighted on the display screen. The terms can be flagged or highlighted as a function of the healthcare provider's respective user profile being processed by data processing apparatus 102 and/or user computing device 104.

Continuing with reference to the flowchart shown in FIG. 4, the healthcare provider "hovers" over a highlighted term for further review (step 406). Information associated with the term automatically appears in the display screen at or near the location of the particular term. In the event that (s)he desires additional information regarding the term, the healthcare provider "clicks" or "taps" his/her mouse or other selection device (e.g., trackball, touchpad, touchscreen or the like), and an additional cascade of information regarding the key term is provided. In the event that more information is desired, the healthcare provider can "click" or "tap" again, and yet an additional cascade of information regarding the key term is provided (steps 408, 410). For example, information that is provided in response to a simple hover-over step is rudimentary and includes only one or two sentences regarding the key term. Information that is provided in response to the first click or other selection is more detailed, and may include symptom information and/or causes and risk factors associated with the key term. Information that is provided in response to one or more additional clicks or other selections is preferably more detailed, and can include diagnostic information, trend information, demographic information or the like. Thus the present application provides for cascades of increasingly detailed information regarding one or more key terms in response to selections or "mouse-clicks" received from a healthcare provider in the graphical user interface. Information associated with the respective cascades can be provided from one or more databases that are stored "locally" on the user's respective computing device 104, can be provided from one or more databases maintained by data processing apparatus 102, and/or can be provided from one or more external databases that are accessible, for example, via data communication network 106 and maintained by one or more third party computing devices.

Continuing with reference to the flowchart shown in FIG. 4, at step 412 an instruction is received from the computing device 104 operated by the healthcare provider that the key term for which the cascades of information have been provided should no longer be flagged or highlighted for the respective user. The key term may be well-learned by the healthcare provider, or the term may not have a bearing on the healthcare provider's practice, and the healthcare provider no longer desires to have the term flagged or highlighted in future medical reports that are provided in the graphical user interface. In response and at step 414, the healthcare provider's user profile is updated to prevent the term from being flagged or highlighted in the graphical user interface in future medical reports.

Thus, as shown and described with reference to FIG. 4, data processing apparatus 102 and/or user computing device 104 can be configured to provide a graphical user interface enabling a user to click once on and/or hover over a key term in a medical record to be provided with a definition associated with the key term. In response to an initial or additional click, additional definition information (such as 2 or 3 sentences) can be provided. Additional options can be provided, such as to enable the user to be provided with causes and risk factors associated with the respective term. In addition, options can be provided for information associated with risk factors that may worsen a disease associated with the key term. Additional selections (e.g., clicks) can be received that inform the graphical user interface to perform one or more additional inquiries, such as to obtain diagnostic evaluation and/or diagnostic criteria information. Additional options and information can be provided in response to additional selections (e.g., clicks), such as to provide information associated with recommended follow-up or treatment, conduct additional searching over a data communication network 106 (e.g., Internet searches), and/or to access one or more Internet websites that provide additional information associated with the key term. Other optional information can include staging are further stratification.

The present application can maintain and/or access one or more databases that, which can be indexed by respective medical terms, that contains, for example, lists of medical diagnoses, procedures, laboratory findings, diagnostic signs and X-Ray findings. In various implementations, other types of information can be provided that relates to or otherwise concerns other industries (e.g., law, construction, automotive, engineering, insurance and/or virtually any other industry). The database(s) preferably does not include uncomplicated words or broad terms, and is instead configured to provide specific terms, complicated terminology, and words that are likely to require a user to otherwise have to access additional definition and elaboration. For example, the database(s) may not include the term, "upper respiratory infection" or "hip fracture," but may contain terms "bronchiolitis" or "intertrochanteric hip fracture," which are items that may deserve further explanation to a primary care physician. By providing this level of detail in the database(s), users are precluded from having to access third-party or external data sources to obtain the information.

As noted above, in one or more implementations user profiles are supported that filter various medical terms to or from the dictionary index, for access to customized information for respective users. Default user profiles can be defined that represent appropriate levels of knowledge or understanding of medical information. For example, a pediatrician is presumed to have a different level of understanding of various medical terms than a neurologist. A user of the present application submits information that represents the user's respective specialty (or lack thereof), and a predefined user profile is assigned for that user. As medical information, such as medical health records, is processed and provided in the graphical user interface, the user's respective user profile configures the application to provide access to detail information that is not presumed to be already known by the user. In addition, the present application supports customizing user profiles, such as by enabling or precluding access to information in the index as the user views a medical record.

For example, a family physician reviews a report from a medical specialist on the physician's computer screen quickly. Any words of possible uncertainty that are included in the dictionary and that are filtered based on the physician's presumed (or customized) knowledge or understanding can be flagged or otherwise highlighted on the display screen. Using a mouse or other selection device, the physician can hover over a highlighted term on which he or she may want further information and then, for example by clicking, tapping or otherwise selecting the term, (s)he starts a cascade that provides further explanation regarding the term. This can include significant amounts of up-to-date research results. Preferably, the cascade of information is provided in a coherent and relatively simple way so as to be concise and relevant to the practice of the family physician. Moreover, in one or more implementations the cascade of information can be presented using one or more algorithms to present the information in a concise, consistent fashion. This avoids a presentation of too much information, and is, therefore, not overly time-consuming for the user to read and digest, and reduces the likelihood of important information being ignored.

In one or more implementations, a software platform integrates with the database(s) to provide a graphical user interface comprising medical terms definitions, and diagnostic and treatment information. The information associated with these sources can be received and processed in various ways, such as via email, fax, SMS, file upload, data import, hard copy and, for example, via optical character recognition ("OCR"), voice recognition or one or more other transcription bases. The software platform can be further provided such that the dictionary is integrated or otherwise provided with medical reports received from various sources, such as referring doctors, medical specialists, laboratories, or the like.

In one or more implementations, one or more data processing apparatuses 102 process information to provide various features and functionality shown and described herein. For example, a medical health record from a radiologist is received by e-mail. The record is received in an ADOBE PDF file format. Thereafter, the record is converted, such as via optical character recognition, into a machine-readable format such as plain text, in order to obtain information in the record. Once information is obtained, a data processing apparatus (and/or a user computing device) is configured to analyze the information to identify one or more terms in the medical record that correspond with data or information stored in one or more databases. As information, such as medical terms, are matched, additional data processing can take place, such as to provide hyperlinks to additional information or to format text in various ways for improved viewing and access.

The graphical user interface provided in accordance with the present application provides, for example, annotations and access to supplemental information associated with one or more records or record sources. For example, a medical health report that is received by a family physician from a radiologist is processed and provided in the graphical user interface. Supplemental information associated with one or more terms in the report is further provided as a function of the graphical user interface. The graphical user interface can be served from a central data computing apparatus 102, which can be presented on user computing devices 104, for example, in standard web browsing software applications. Alternatively, the graphical user interface can be provided in a "client" software application, such as a mobile app that runs on a smartphone or on other software configured with a user computing device 104.

In one or more implementations, the present application provides for and/or improves delivery of primary care medicine, and improves the likelihood of improved outcomes for patients. The teachings herein to empower healthcare providers, such as primary care physicians, family doctors, primary care internists and pediatricians, by providing accurate and current information in timely ways. Such information, including detailed medical information, can be made instantly accessible by harnessing data presented to the healthcare provider, such as from specialist consults, blood results, radiology results and other laboratory test results, to assist the healthcare provider quickly and virtually effortlessly to utilize the data. This reduces or eliminates uncertainty, such as relating to an academic word, a complicated diagnosis or laboratory or radiographic abnormality, and immediately presents an explanation clearly and concisely.

The present application utilizes a systems-based approach that includes technology to receive and process information, and to provide a graphical user interface that enables to define medical terminology quickly, present causes and risk factors, aid in establishing proper diagnoses and direct users of the application, such as healthcare providers, to relevant but simplified information necessary for the user's respective practice. As noted herein this can involve use of OCR technology, and search engine and data mining systems. This information can be presented as a function of hyperlinks, such as in a form with quick access, and to be essentially effortless for the primary care physician to obtain.

In one or more implementations, a document presented to a user computing device originates from a number of different sources, including but not limited to: "local" storage (e.g., a hard drive, flash drive, CD, DVD, BLU-RAY or other storage media connected to or directly assessable by the user's computing device); "remote" storage (e.g., via a terminal services session, such as Citrix or remote desktop); "browser-based access" (e.g., such as via INTERNET EXPLORER, MOZILLA FIREFOX, OR GOOGLE CHROME); and other "remote" storage access (e.g., via a JAVA window that provides information from a remote server application). An "original" healthcare record document may be formatted in various ways, such as a .DOC, .PDF, .TXT, as well as an image file, such as a JPG, TIFF, scanned image file, facsimile or document. For a user's convenience, the general appearance of the captured document can be maintained such as to preserve, for example, indentation, paragraph formatting, punctuation, and/or graphical features, such that the captured file can be reproduced to have the same overall appearance as the file that was originally received. Moreover, the original file that is captured, for example, from a user's computing device can be saved in a generic (i.e., common) format, such as PDF, which enables the captured document to be processed at a later time. In one or more implementations, the original file can be processed in such a manner that "hovering-over" special words results in an instruction being generated to cause a graphical screen control, such as a popup textbox, to appear that provides definitions or other useful information associated with particular words.

Further, the present application can be configured to save a copy of the original document, such as in a common format, to provide much of the functionality shown and described herein. Thereafter, a user can access newly saved file, such as the PDF file, and enjoy the functionality set forth in the processed file. For example, special words that are filtered as a function of the user's profile can be formatted, such that when the user "hovers" over the particular words, a "popup" textbox appears that provide definitions or other useful information associated with the particular words. This feature of the present application alleviates a need for a recipient to use a client software application for functionality, such as shown and described herein. In one or more implementations, various files that are received from a plurality of parties can be processed in accordance with the teachings herein to provide "compiled" files (e.g., PDF files) that include additional information and functionality.

The teachings herein improve the academic and financial efficiency of the medical provider system. Using the teachings herein, primary care physicians are able to extract and analyze medical data from multiple sources and locations, and most importantly, be provided this information in an effortless manner. This can occur as a function of a computer program operating on one or more computing devices that analyze an abnormality, gather data from patient's medical records and execute an algorithm to assist with making a diagnosis. In addition, results of tests that have been previously done can be presented, which further helps a primary care physician and/or other medical care provider.

In one or more implementation, data processing apparatus 102 and/or user computing device 104 are configured to compare words in a processed medical record to terms that are stored in an indexed list and that correlate to a user's respective user profile. When matches are identified, the word(s) are displayed in a highlighted and/or hyperlinked format. When the user clicks on the word, the application presents the user with related information obtained from a medical dictionary either, for example, via SQL queries or Internet search.

Figure 5:
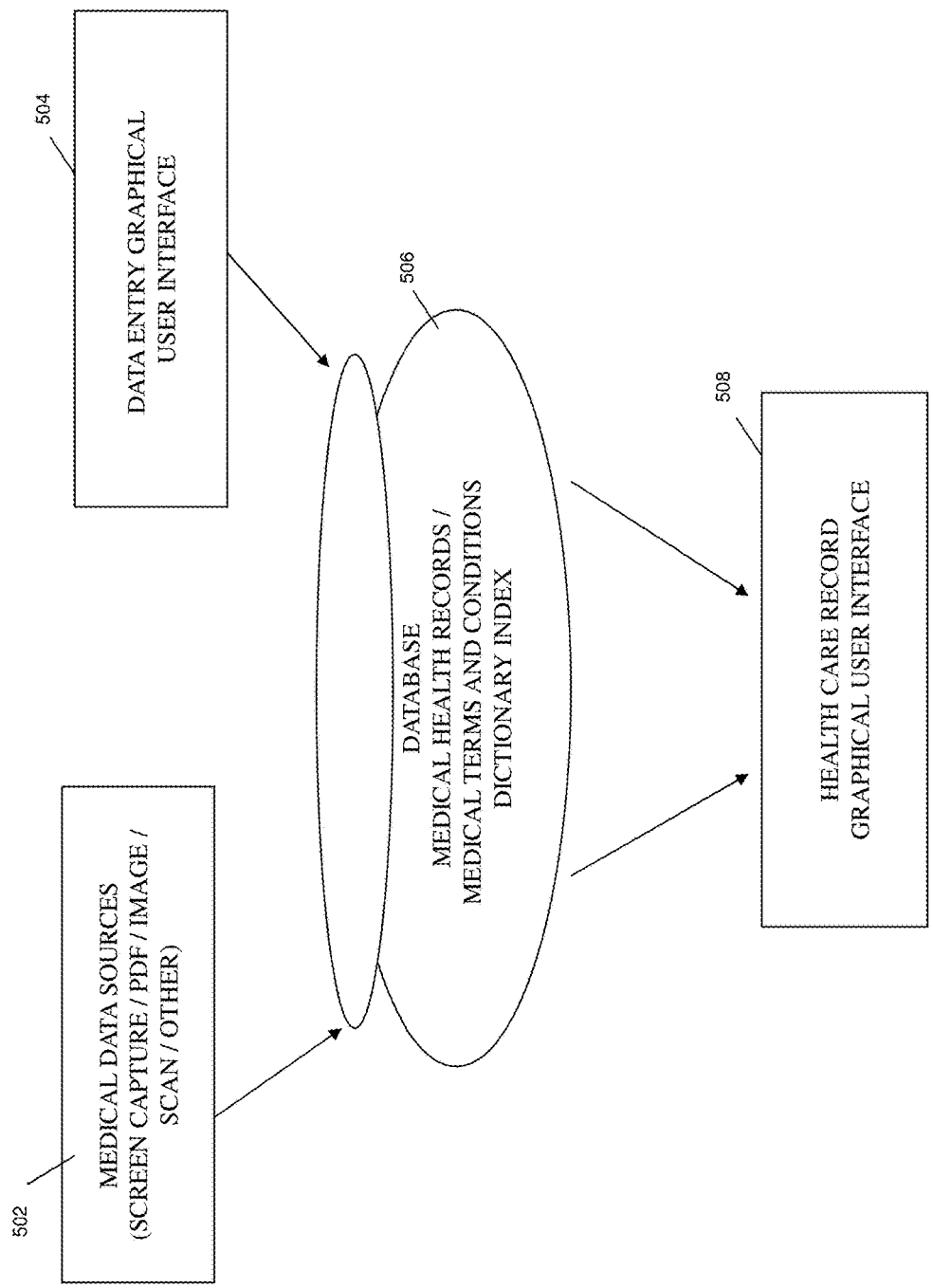
FIG. 5 is a block diagram that illustrates data sources, database(s) and graphical user interface(s), such as shown and described herein, for providing functionality in accordance with the present application.

The present application is useful for and or compatible with developed electronic healthcare record systems, and can target individual practices for particular and contextual use. FIG. 5 is a block diagram that illustrates data sources 502, 504, database 506 and graphical user interface 508, such as shown and described herein, for providing functionality in accordance with the present application. Information can be mined and/or accessed, for example as a function of OCR and voice recognition technology, search engines and other known data mining systems (data sources 502). Information can be entered via a data entry graphical user interface 504, such as pertaining to complex medical terminology associated with procedures, diagnoses or the like. Database 506 is configured to store information received from sources 502 and interface 504, and to present the information in a meaningful and efficient way, such as via healthcare record graphical user interface 508. Electronic healthcare records can be processed and provided with respective hyperlinks for quick access to information, and be essentially effortless for the user to obtain detailed information in seconds.

Figure 6:
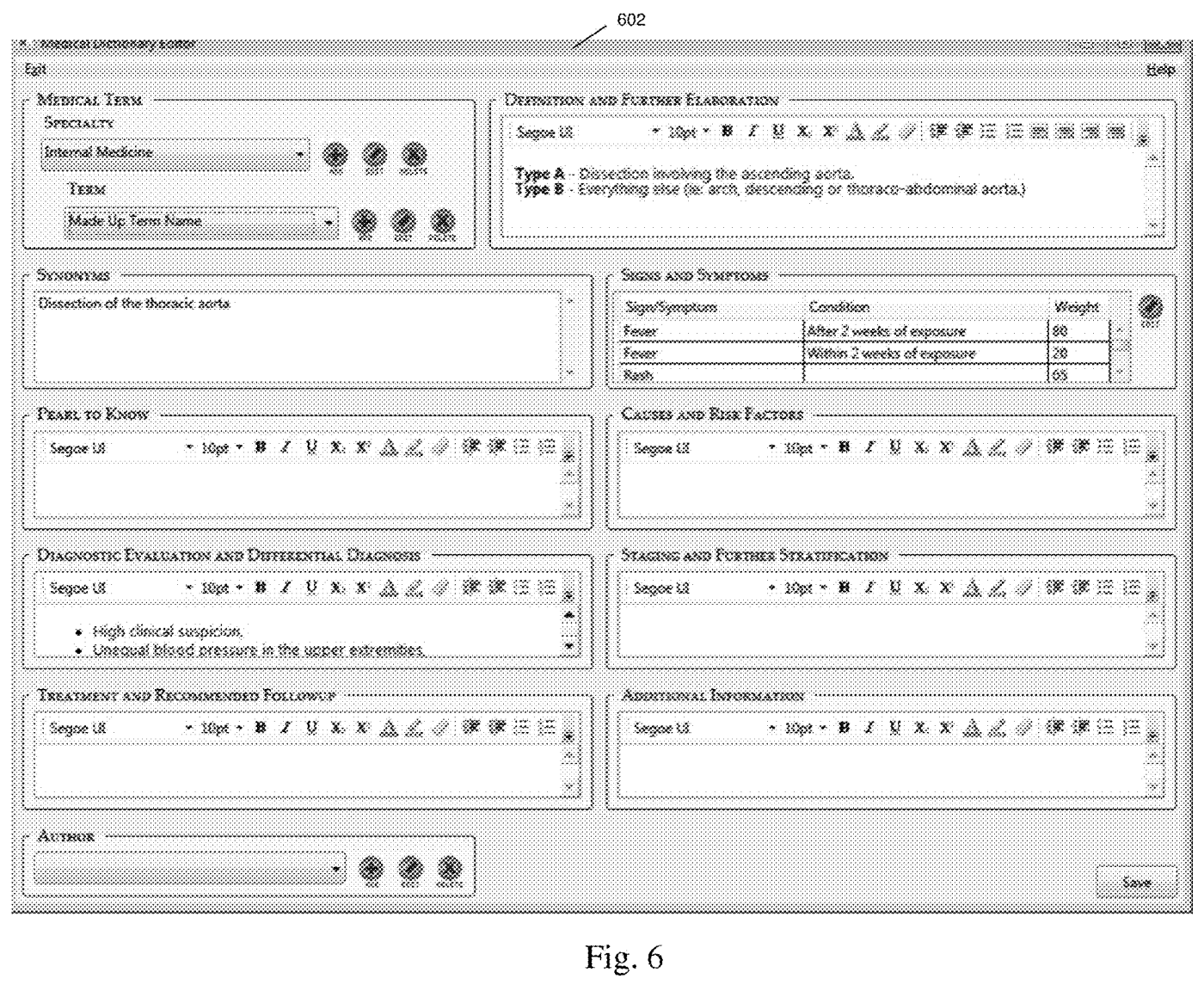

FIG. 6 illustrates an example data entry display screen 602 that is configured for users to enter information associated with medical terms in accordance with an implementation of the present application. In the example shown in FIG. 6, the respective term regards dissection involving the ascending aorta. Referred to herein, generally, as a "medical dictionary editor," data entry display screen 602 is organized in sections for users to identify a respective medical term, submit information regarding a definition and elaboration, synonyms, signs and symptoms, additional information ("Pearl") to know, causes and risk factors, diagnostic evaluation and differential diagnosis, staging and further stratification, treatment and recommended follow-up, and additional information. An option is further provided for the user to identify the author of the information.

Figure 7:
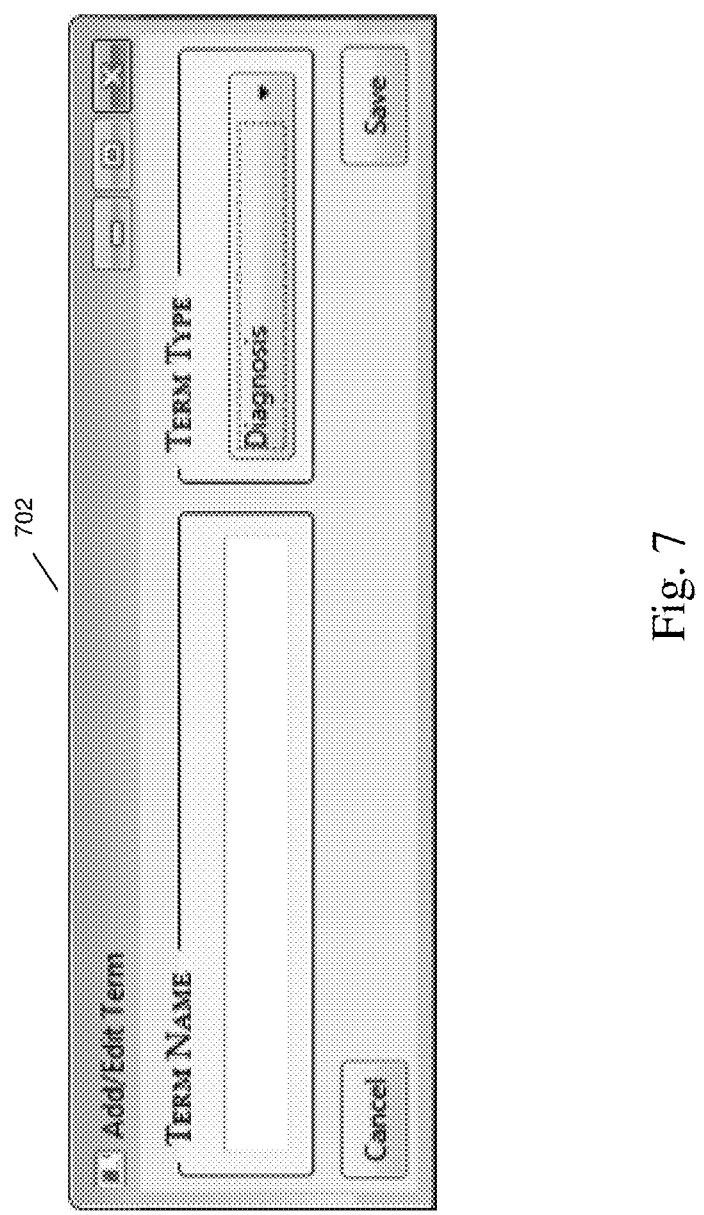
FIG. 7 illustrates an example data entry display screen that is configured for users to enter information associated with medical terms in accordance with an implementation of the present application.

FIG. 7 illustrates an example data entry display screen 702 that is configured for users to enter information associated with medical terms in accordance with an implementation of the present application. Using graphical screen control set forth in FIG. 7, users can add/edit a term and associate the term with a particular type. For example, a user can enter a new medical term, anticardiolipin syndrome, in data entry display screen 702. Using a graphical screen control, e.g., a drop-down list, the user can select the term type as a "diagnosis." Additional information associated with this diagnosis can be provided, such as shown and described above.

Figure 8:
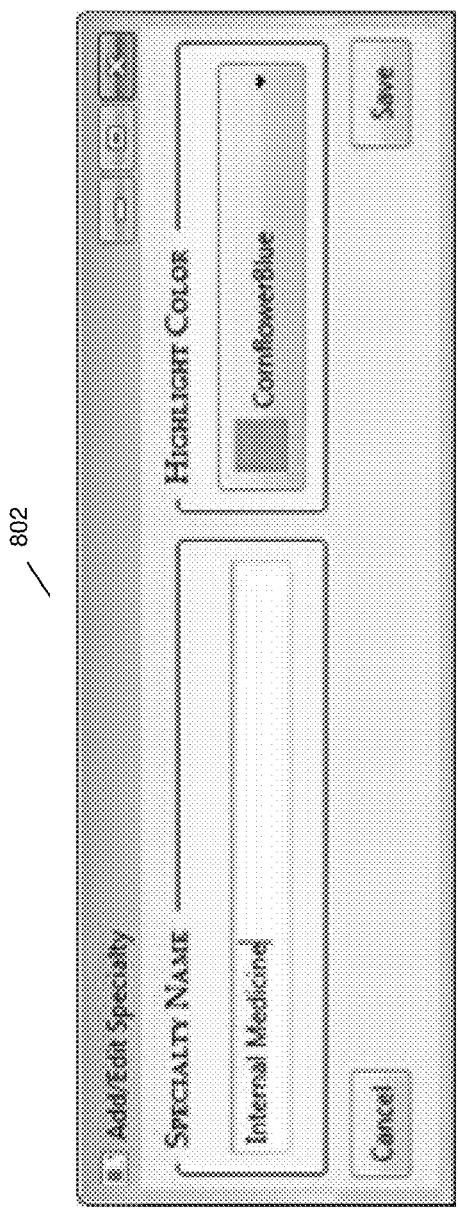
FIG. 8 illustrates an example data entry display screen that is configured for users to enter information associated with medical specialties in accordance with an implementation of the present application.

FIG. 8 illustrates an example data entry display screen 802 that is configured for users to enter information associated with medical specialties in accordance with an implementation of the present application. For example, a medical specialist can use data entry controls provided in data entry display screen 802 to and and/or edit a specialty name. Moreover, data entry display screen 802 includes an option to define a highlight color for all terms that correspond to a selected specialty. For example, when a user accesses a graphical user interface that includes a medical record that is configured with flagged and/or highlighted terms pursuant to definitions set forth in FIG. 8, all terms that correspond with the specific specialty are highlighted in the color that corresponds with the defined color in FIG. 8 (e.g., cornflower blue). This is a particularly useful feature of the present application such that a user viewing a record, such as a medical record that is replete with terms associated with various medical specialties, and identify at a glance particular terms that correspond to particular medical specialties. Moreover, information can be color-coated to represent sources of information. For example information that is entered in one or more databases via a graphical user interface may be color coded to be brown, while information that is received outside data sources and processed in accordance with the teachings herein may be color-coded blue.

Figure 9:
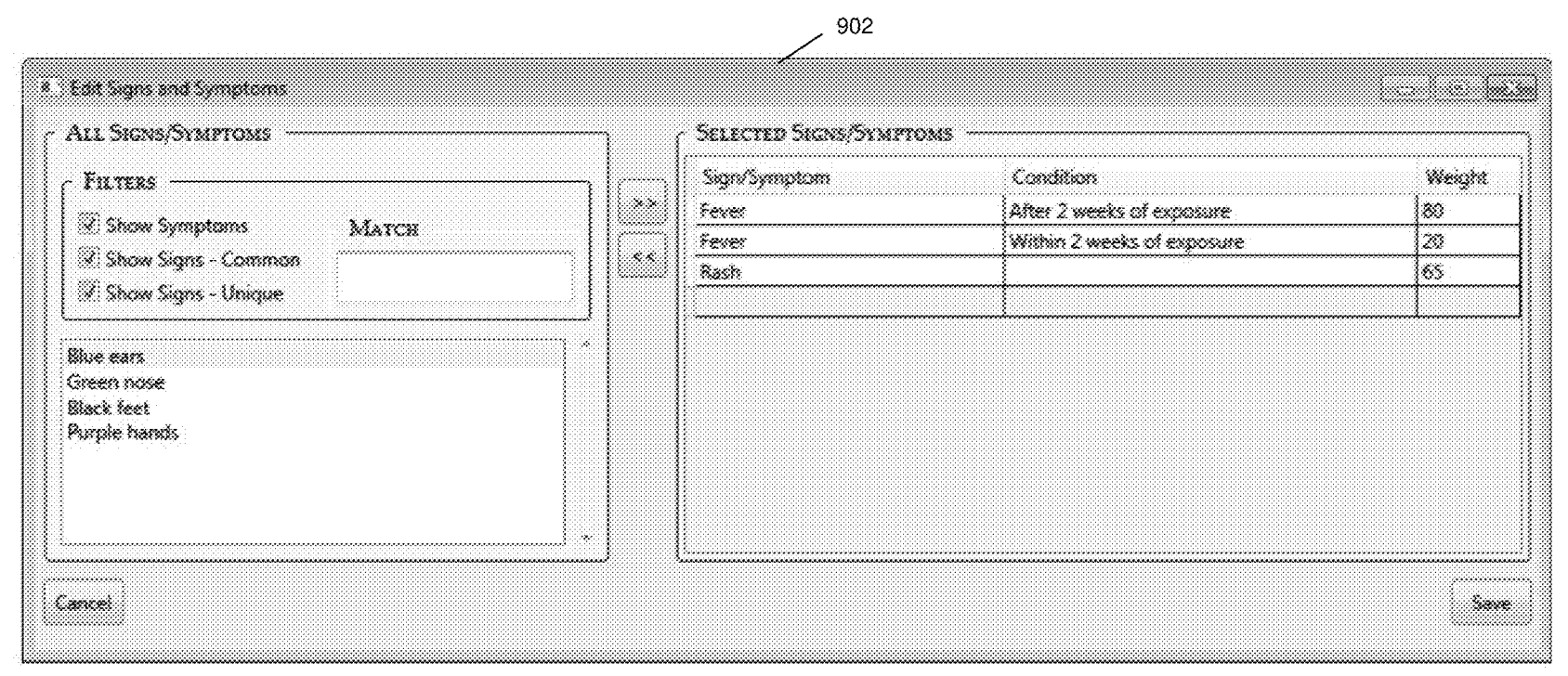

FIG. 9 illustrates an example data entry display screen 902 that is configured for users to add and edit information associated with signs and symptoms that are associated with a respective medical term. In the example shown in FIG. 9, the selected sign/symptom is a fever that is associated with dissection involving the ascending aorta. In the data entry display screen 902, filters are provided for showing symptoms, common signs and/or unique signs. Moreover, a table listing symptoms and signs is displayed and include blue ears, green nose, black feet and purple hands. Additionally, weighted values are provided for a fever after two weeks of exposure (80), a fever within two weeks of exposure (20) and a rash (65). When the user is satisfied with his or her selections, the user can save the entries, such as to a SQL database by selecting "save" button. The weighting factors can be used to indicate a significance of a sign/symptom with regard to a specific condition or diagnosis. Using the data entry display screen 902, signs and symptoms are associated with a condition or diagnosis.

Thus, as shown and described above, data processing apparatus 102 and/or user computing devices 104 can be configured for users to search for, add, delete or edit the database of medical terms provided as a function of data entry graphical user interface 502 (FIG. 5). Users can add new medical terms and/or edit previously entered information associated with a medical term. Further, authorized users can delete selected medical term(s) from the database, and/or clear data entry performed at a certain point in time. In one or more implementations, graphical screen controls can be provided to enable a user to navigate the database, such as alphabetically, as a function of one or more navigation controls provided data entry display screen 502. Furthermore, the interface provided in accordance with example implementations is designed to be seamless to the end user, and provide for scalable data storage. As the amount of data increases, the ability for the tool to be utilized to better provide information to healthcare professionals increases exponentially as well.

FIGS. 10-13 illustrate an example implementation of healthcare record graphical user interface 508 in accordance with an implementation. FIG. 10, for example illustrates healthcare record 1000 in the form of a letter from one physician to another physician regarding a respective patient, Louis, and that is provided in graphical user interface 508. In the example shown in FIG. 10, the diagnosis prothrombin gene mutation, heterozygous, is highlighted in the electronic record, which indicates additional functionality provided by data processing apparatus 102 and/or user computing device 104.

Figure 11:
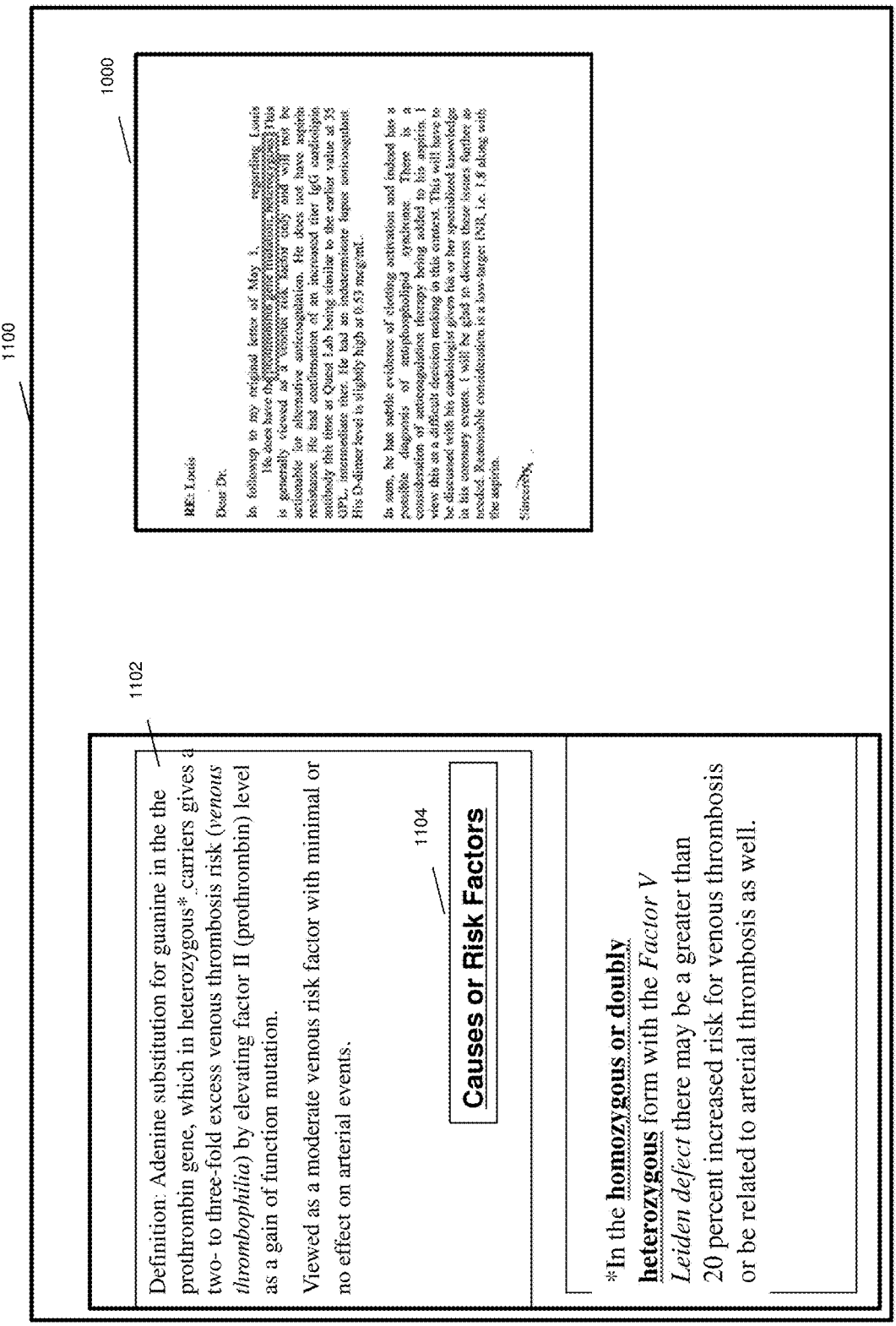

FIG. 11 illustrates an example display screen 1100 that includes the health record 1000, and definition display section 1102. Definition display section 1102 may be provided, for example, as the user viewing display screen 1100 hovers his or her mouse over the highlighted diagnosis. Alternatively, the definition display section 1102 may be provided upon receiving a click or other selection associated with the user computing device 104. Additionally, causes or risk factors option 1104 is provided for displaying additional information associated with causes or risk factors for the selected diagnosis. Upon selection of the causes or risk factors option 1104, additional information can be provided.

Figure 12:
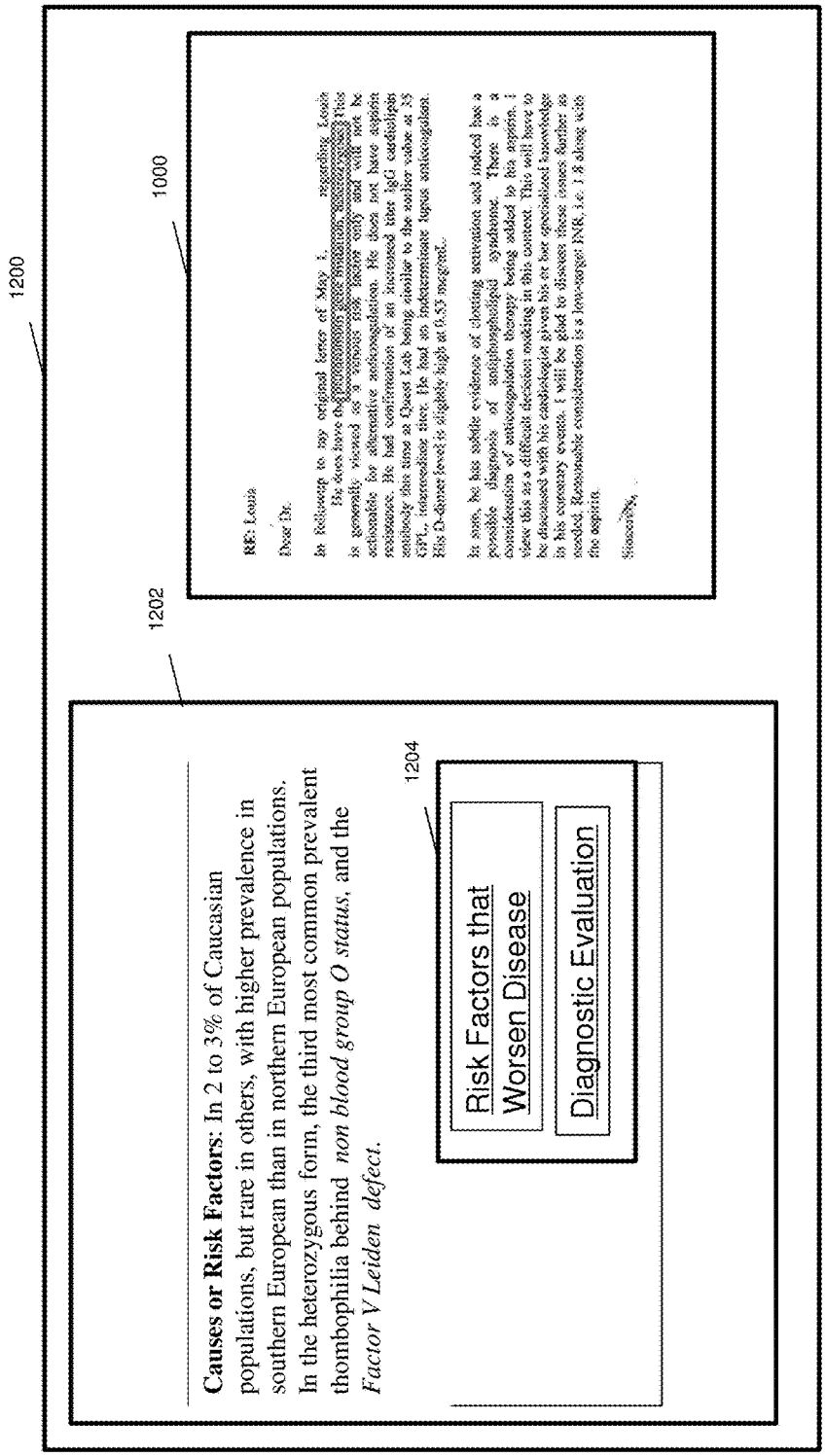

FIG. 12 illustrates an example display screen 1200 that includes the health record 1000, and causes or risk factors display section 1202, which identifies demographic information, blood types and/or other information associated with causation and/or risk. In addition, risk factors that worsen the disease and/or diagnostic evaluation option 1204 is displayed that, when selected, results in additional information being displayed associated with worsening risk factors and/or diagnostic evaluations.

FIG. 13 illustrates an example display screen 1300 that includes the health record 1000, and risk factors that worsen disease display section 1302. Risk factors that worsen disease display section 1302 identifies additional risks that could result in worsening disease associated with the highlighted term in the medical record 1000.

Thus and as shown and described above with reference to FIGS. 10-13, a graphical user interface 508 is provided that includes medical records that are displayed and reformatted to provide information and options associated with technical terms. Information that can be provided in association with a respective term can include, for example, definitions, causes or risk factors, diagnostic evaluations, clinical and/or laboratory criteria, and/or recommended treatments.

The present application uses information technology to provide quick and coherent access to complicated information in a clear interface that aids, for example, in medical diagnosis, evaluation and treatment. Cascades of information are presented in utilizing one or more algorithms, which may depend upon a diagnosis, and abnormal laboratory finding, a diagnostic sign or X-Ray finding or one or more symptoms. Depending upon a starting point, causes or risk factors, relevance and differential differences, can be provided to the user, as well as how to make a diagnosis or to provide further diagnostic evaluation and interpretation information. Physicians and other healthcare professionals greatly benefit from the functionality shown and described herein, and the present application improves upon academic and financial efficiency in the medical provider system. The present application extracts and analyzes medical data from multiple sources and provides information in an effortless manner for the healthcare provider.

As noted above, although many of the examples and descriptions herein regard the medical industry, the present application is not so limited. Using the teachings herein, many other industries can benefit using the technological improvements provided herein.

Furthermore, it is recognized herein that patient privacy rights and information associated with diagnoses and treatment may require specific security measures, such as for legal compliance. In one or more implementations of the present application, patient privacy is protected by managing sensitive information, such as in a reserved portion of an Internet web client software application operating on user computing device 104, or via security provided by data processing apparatus 102. For example, information can be encrypted and stored securely on a local client device and/or a server computing device to ensure that patient privacy is maintained, such as in compliance with the Health Insurance Portability and Accountability Act ("HIPAA").

Although much of the foregoing description has been directed to systems and methods for code processing, the systems and methods disclosed herein can be similarly deployed and/or implemented in scenarios, situations, and settings far beyond the illustrated scenarios.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and arrangements of the present systems and methods provide a computer implemented method, computer system, and computer program product for processing code(s). The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. An apparatus, comprising:
    at least one database accessible to at least one processor, the at least one database including:
        electronic medical records including information associated with one or more of medical diagnoses, treatments and evaluations of respective patients;
        electronic user profile information associated with respective users and representing corresponding degrees understanding of medical information for each of the respective users; and
        electronic medical information including information associated with medical terminology respectively associated with at least some of the diagnoses, treatments and evaluations;
    a user interface module configured with at least one processor to provide prompts for information associated with the electronic medical information, to receive responses to the prompts from a first respective user, and to store the responses in the at least one database;
    an electronic medical record generation module configured with at least one processor that is configured to:
        access a first electronic medical record;
        generate a first working copy of the first electronic medical record, wherein the first electronic medical record exists separately from the first working copy;
        transform at least some content of the first working copy of the electronic medical record into digitized text and replace the at least some content in the first working copy of the electronic medical record with the digitized text;
        correlate at least some of the digitized text as a function of some of the electronic profile information that is associated with the first respective user, wherein the at least some of the digitized text represents at least one diagnosis, treatment and evaluation;

filter some of the electronic medical information to provide corresponding electronic medical information that is associated with the correlated at least some of the digitized text;

transform the correlated at least some of the digitized text to selectable digitized text;

display at least a first portion of the corresponding electronic medical information automatically in response to a pointer hovering over at least some of the selectable digitized text;

subsequent to the hovering, display at least a second portion of the corresponding of electronic medical information in response to a first selection of the at least some of the selectable digitized text;

subsequent to the first selection, display at least a third portion of the corresponding of electronic medical information in response to a second selection of the at least some of the selectable digitized text; and compile the filtered electronic medical information with the first working copy of the first electronic medical record into a single file, wherein, the electronic medical record generation module is further configured to generate a different second working copy of the electronic medical record for a second user having a different electronic user profile information, wherein the second working copy of the electronic medical record includes at least some different digitized text than the first working copy of the electronic medical record, and further wherein the second working copy of the electronic medical record is integrated with at least some filtered electronic medical information that is different from the corresponding of electronic medical information.

2. The apparatus of claim 1, wherein the electronic medical record generation module is further configured to select a different user profile information.

3. The apparatus of claim 1, wherein the electronic medical record generation module is further configured with at least one selectable option to customize user profile information associated with the first and/or second user.

4. The apparatus of claim 1 wherein the user interface module is further configured to provide prompts for information associated with at least one of medical terms, definitions, signs and symptoms, risk factors, causes, diagnostic evaluations, staging, treatment and follow-up procedures.

5. The apparatus of claim 4, wherein the user interface module is further configured to associate at least one medical term with a corresponding type.

6. The apparatus of claim 1, wherein the user interface module is further configured to: prompt for information associated with a specialty, to prompt for information associated with a corresponding color coding of the specialty;

to receive responses to the respective prompts; and to store the responses to the respective prompts in the at least one database.

7. The apparatus of claim 6, wherein the electronic medical record generation module is further configured to display at least one medical term in a corresponding color code associated with a specialty that corresponds with the at least one medical term.

8. The apparatus of claim 1, wherein the user interface module is further configured to:

prompt for information associated with signs and symptoms associated with a respective medical term;

to prompt for at least one filter associated with a sign and/or symptom;

to receive at least one response to a prompt for the at least one filter; and to store the response to the prompt for the at least one filter in the at least one database.

9. The apparatus of claim 8, wherein the electronic medical record generation module is further configured to access filter information in the at least one database, and to display sign and symptom information associated with a selected medical term in accordance with the access to filter information.

10. The apparatus of claim 1, wherein the electronic medical record generation module is further configured to provide cascades of information, and further wherein cascades of information include at least one of definitions, causes, risk factors, risk factors that worsen a disease, and diagnostic information.

11. A code processing method, comprising:

accessing, by at least one processor, at least one database that includes:

electronic medical records including information associated with one or more of medical diagnoses, treatments and evaluations of respective patients;

electronic user profile information associated with respective users and representing corresponding degrees understanding of medical information for each of the respective users; and electronic medical information including information associated with medical terminology respectively associated with at least some of the diagnoses, treatments and evaluations;

providing, by at least one processor, a first user interface configured to provide prompts for information associated with the electronic medical information, to receive responses to the prompts from a first respective user, and to store the responses in the at least one database;

accessing, by at least one processor, a first electronic medical record;

generating, by at least one processor, a first working copy of the first electronic medical record, wherein the first electronic medical record exists separately from the first working copy;

transforming, by at least one processor, at least some content of the first working copy of the electronic medical record into digitized text and replace the at least some content in the first working copy of the electronic medical record with the digitized text;

correlating, by at least one processor, at least some of the digitized text as a function of some of the electronic profile information that is associated with the first respective user, wherein the at least some of the digitized text represents at least one diagnosis, treatment and evaluation;

filtering, by at least one processor, some of the electronic medical information to provide corresponding electronic medical information that is associated with the correlated at least some of the digitized text;

transforming, by at least one processor, the correlated at least some of the digitized text to into selectable digitized text;

displaying, by at least one processor, at least a first portion of the corresponding electronic medical information automatically in response to a pointer hovering over at least some of the selectable digitized text;

subsequent to the hovering, displaying, by at least one processor, at least a second portion of the corresponding of electronic medical information in response to a first selection of the at least some of the digitized text;

displaying, by at least one processor, at least a third portion of the corresponding of electronic medical information in response to a second selection of the at least some of the digitized text;

compiling, by at least one processor, the filtered electronic medical information with the first working copy of the first electronic medical record into a single file, and generating, by at least one processor, a different second working copy of the electronic medical record for a second user a different electronic user profile information, wherein the second working copy of the electronic medical record includes at least some different digitized text than the first working copy of the electronic medical record, and further wherein the second working copy of the electronic medical record is integrated with at least some filtered electronic medical information that is different from the corresponding of electronic medical information.

12. The method of claim 11, further providing, by at least one processor, at least one selectable option to augment or select different user profile information.

13. The method of claim 11, further providing, by at least one processor, at least one selectable option to customize user profile information associated with the first and/or second user.

14. The method of claim 11 wherein the first user interface is further configured, by at least one processor, to provide prompts for information associated with at least one of medical terms, definitions, signs and symptoms, risk factors, causes, diagnostic evaluations, staging, treatment and follow-up procedures.

15. The method of claim 14, wherein the first user interface is further configured, by at least one processor, to associate at least one medical term with a corresponding type.

16. The method of claim 11, wherein the first user interface is further configured, by at least one processor, to:
prompt for information associated with a specialty,
to prompt for information associated with a corresponding color coding of the specialty;
to receive responses to the respective prompts; and
to store the responses to the respective prompts in the at least one database.

17. The method of claim 16, further providing, by at least one processor, displaying at least one medical term in the processed electronic medical record according to a corresponding color code associated with a specialty that corresponds with the at least one medical term.

18. The method of claim 11, wherein the first user interface is further configured, by at least one processor, to:
prompt for information associated with signs and symptoms associated with a respective medical term;
to prompt for at least one filter associated with a sign and/or symptom;
to receive at least one response to a prompt for the at least one filter; and
to store the response to the prompt for the at least one filter in the at least one database.

19. The method of claim 18, further providing, by at least one processor, accessing filter information in the at least one database, and to display sign and symptom information associated with a selected medical term in accordance with the access to filter information.

20. The method of claim 11, further providing, by at least one processor, cascades of information in response to sequential selections from a user, and further wherein cascades of information include at least one of definitions, causes, risk factors, risk factors that worsen a disease, and diagnostic information.

* * * * *